US008696855B2

(12) United States Patent
Ellingson et al.

(10) Patent No.: US 8,696,855 B2
(45) Date of Patent: Apr. 15, 2014

(54) SIMPLIFIED ABSORBENT ARTICLE CONSTRUCTION AND METHOD OF MAKING

(75) Inventors: Daniel Lee Ellingson, Appleton, WI (US); Alissa Rachel Ellingson, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 294 days.

(21) Appl. No.: 12/500,981

(22) Filed: Jul. 10, 2009

(65) Prior Publication Data

US 2011/0005670 A1 Jan. 13, 2011

(51) Int. Cl.
*B26F 1/00* (2006.01)

(52) U.S. Cl.
USPC ........... 156/257; 156/270; 156/253; 156/264; 156/265; 156/268; 156/299

(58) Field of Classification Search
CPC ................... A61F 13/15723; A61F 13/15747; A61F 13/15804; A61F 13/15739; B26D 1/025; B26D 3/085; B26F 1/00
USPC ......... 156/253, 269, 270, 264, 256, 299, 257, 156/268, 265; 15/244.4; 225/94
See application file for complete search history.

(56) References Cited

U.S. PATENT DOCUMENTS

| | | | |
|---|---|---|---|
| 1,340,225 A * | 5/1920 | Howard | 225/2 |
| 1,723,303 A | 8/1929 | Schwartz | |
| 1,778,270 A * | 10/1930 | Miller | 428/316.6 |
| 2,009,310 A | 7/1935 | Dendoff | |
| 2,366,002 A | 12/1944 | Carden | |
| 2,652,087 A * | 9/1953 | Turpin | 83/762 |
| 2,931,361 A | 4/1960 | Sostrin | |
| 3,049,228 A | 8/1962 | Burnett | |
| 3,359,980 A | 12/1967 | Rosenblatt | |
| 3,431,908 A | 3/1969 | Lee | |
| 3,527,221 A | 9/1970 | Croon et al. | |
| 3,578,155 A | 5/1971 | Small et al. | |
| 4,610,682 A | 9/1986 | Kopp | |
| 5,755,706 A * | 5/1998 | Kronenthal et al. | 604/358 |
| 6,051,094 A | 4/2000 | Melbye et al. | |
| 6,521,320 B2 | 2/2003 | McCabe et al. | |
| 6,652,701 B1 * | 11/2003 | Boulanger | 156/267 |
| 7,160,408 B2 | 1/2007 | Otsubo | |
| D572,910 S | 7/2008 | Schreiner | |
| 2005/0113793 A1 | 5/2005 | Bianco | |
| 2008/0281286 A1 | 11/2008 | Petersen | |
| 2008/0300565 A1 * | 12/2008 | Takahashi et al. | 604/367 |

FOREIGN PATENT DOCUMENTS

| | | |
|---|---|---|
| GB | 1 114 255 A | 5/1968 |
| WO | WO 83/04163 A1 | 12/1983 |
| WO | WO 02/32360 A2 | 4/2002 |
| WO | WO 02/32361 A2 | 4/2002 |

\* cited by examiner

*Primary Examiner* — Linda L. Gray
(74) *Attorney, Agent, or Firm* — Kimberly-Clark Worldwide, Inc.

(57) ABSTRACT

A method includes moving an absorbent composite in a machine direction, severing the composite at a first cut oriented in a direction that is non-parallel and non-perpendicular with the machine direction, severing the composite at a second cut oriented in a direction that is non-parallel and non-perpendicular with the machine direction, severing the composite at a third cut oriented in a direction that is perpendicular to the machine direction, and separating the composite along the first cut, the second cut, and the third cut into discrete absorbent articles.

20 Claims, 10 Drawing Sheets

SIMPLIFIED ABSORBENT ARTICLE CONSTRUCTION AND METHOD OF MAKING

BACKGROUND OF THE INVENTION

The use of disposable absorbent articles has become commonplace in many parts of the world. As use of these articles has continued to mature, the features, performance, and manufacturing complexity have continued to increase. While these advancements have resulted in aesthetically pleasing, high performance absorbent articles, the capital investment and manufacturing costs have also increased. While these advances and sophisticated absorbent articles are welcomed in many segments of society, there is also a need for a more simplified absorbent article to meet the basic needs of lower income consumers in various markets around the world.

SUMMARY OF THE INVENTION

In order to fulfill the basic needs of a more simplified absorbent article, the present invention provides a method for making multiple absorbent articles. The method includes the steps of providing a rectangular liquid-impermeable layer having a first length and a first width; providing an absorbent layer having a second length and a second width; and joining the absorbent layer and the liquid-impermeable layer in facing relation to define an absorbent composite. The method further includes severing the absorbent composite at a first cut oriented in a first direction, wherein the first direction is non-parallel with the first width or the first length and severing the absorbent composite at a second cut oriented in a second direction, wherein the second direction is non-parallel with the first width or the first length, and wherein the second cut intersects the first cut. Finally, the method includes separating the composite along the first cut and the second cut into discrete absorbent articles.

In some embodiments of this aspect, the composite is completely severed by the first cut and the second cut to define four discrete absorbent articles having a common junction point. In some embodiments, at least one of the first cut and the second cut form a line of weakness but are not completely severed.

In some embodiments, the first length may be equal to the second length and the first width may be greater than second width. In some embodiments, the absorbent layer may be centered relative to the liquid-impermeable layer. In some embodiments, the first length may be greater than the second length and the first width may be greater than the second width and the absorbent layer may be centered relative to the liquid-impermeable layer.

In some embodiments, the four discrete absorbent articles may include a first pair of absorbent articles having a first configuration and a second pair of absorbent articles having a second configuration wherein the first configuration and the second configuration are different. In various embodiments, the first configuration may have a first absorbent capacity and the second configuration may have a second absorbent capacity that is greater than the first absorbent capacity.

In some embodiments, the absorbent layer and the liquid-impermeable layer may be joined in facing relation to define an overlap region and the method may further include the steps of removing a first cut out, a second cut out, a third cut out, and a fourth cut out from the overlap region of the composite to define a first opening, a second opening, a third opening, and a fourth opening. The method may further include severing the liquid-impermeable layer wherein two of the first opening, the second opening, the third opening, and the fourth opening span only the first cut and wherein two of the first opening, the second opening, the third opening, and the fourth opening span only the second cut. In various embodiments, the method further includes the step of centering the first cut out, the second cut out, the third cut out, and the fourth cut out on the first cut or the second cut.

In another aspect, the present invention provides a method for making multiple absorbent articles. The method includes moving a web of absorbent composite material in a machine direction. The absorbent composite material includes a liquid-impermeable layer joined in facing relation with an absorbent material layer to define an overlap region. The method includes severing the liquid-impermeable layer and the absorbent layer at a first cut oriented in a first direction, wherein the first direction is non-parallel and non-perpendicular with the machine direction. The method further includes severing the liquid-impermeable layer and the absorbent layer at a second cut oriented in a second direction, wherein the second direction is non-parallel and non-perpendicular with the machine direction and wherein the second cut intersects the first cut at a single intersection. The method also includes severing the liquid-impermeable layer and the absorbent layer at a third cut oriented in a third direction, wherein the third direction is perpendicular or substantially perpendicular to the machine direction. Finally, the method includes separating the composite along the first cut, the second cut, and the third cut into discrete absorbent articles.

In various embodiments of this aspect, the absorbent material may be provided in discrete pieces and may be joined in facing relation with the liquid-impermeable layer to define overlap regions and open regions and the method may include severing the open regions with the third cut.

In some embodiments the absorbent material may be provided in discrete pieces and may be joined in facing relation with the liquid-impermeable layer to define overlap regions and open regions and the method may further include the steps of removing a first cut out, a second cut out, a third cut out, and a fourth cut out from the absorbent composite in the overlap region, to define a first opening, a second opening, a third opening, and a fourth opening. The method also includes orienting the first cut such that two of the first opening, the second opening, the third opening, and the fourth opening span only the first cut and orienting the second cut such that two of the first opening, the second opening, the third opening, and the fourth opening span only the second cut. Finally, the method includes orienting the third cut to align with the open regions.

In some embodiments, the composite may be completely severed by the first cut, the second cut, and the third cut to define four discrete absorbent articles having a common junction point wherein the four discrete absorbent articles comprise a first pair of absorbent articles having a first configuration and a second pair of absorbent articles having a second configuration wherein the first configuration and the second configuration are different. In some embodiments, the first configuration may have a first absorbent capacity and the second configuration may have a second absorbent capacity greater than the first absorbent capacity.

In another aspect, the present invention provides a method for making multiple absorbent articles. The method includes moving a web of absorbent composite material in a machine direction. The absorbent composite material includes a liquid-impermeable layer joined in facing relation with an absorbent material layer to define an overlap region. The method further includes removing a first cut out, a second cut out, a third cut out, and a fourth cut out from the overlap region of the absorbent composite to define a first opening, a second opening, a third opening, and a fourth opening. The method also includes severing the liquid-impermeable layer and the absorbent layer at a first cut oriented in a first direction wherein the first direction is non-parallel and non-perpendicular with the machine direction and wherein the first cut completely severs both the absorbent layer and the liquid-impermeable layer and wherein two of the first opening, the second opening, the third opening, and the fourth opening span only the first cut. The method also includes severing the liquid-impermeable layer and the absorbent layer at a second cut oriented in a second direction wherein the second direction is non-parallel and non-perpendicular with the machine direction and wherein the second cut intersects the first cut and wherein two of the first opening, the second opening, the third opening, and the fourth opening span only the second cut. The method also includes severing the liquid-impermeable layer and the absorbent layer at a third cut oriented in a third direction, wherein the third direction is perpendicular to the machine direction. Finally, the method includes separating the composite along the first cut, the second cut, and the third cut into discrete absorbent articles.

In various embodiments, the absorbent material may be provided in discrete pieces and may be joined in facing relation with the liquid-impermeable layer to define overlap regions and open regions wherein the method includes severing the open regions with the third cut.

In some embodiments, the composite may be completely severed by the first cut, the second cut, and the third cut to define four discrete absorbent articles having a common junction point. In various embodiments at least one of the first cut and the second cut form a line of weakness but are not completely severed.

The four discrete absorbent articles may include a first pair of absorbent articles having a first configuration and a second pair of absorbent articles having a second configuration wherein the first configuration and the second configuration are different. In some embodiments, the first configuration may have a first absorbent capacity and the second configuration may have a second absorbent capacity greater than the first absorbent capacity.

DETAILED DESCRIPTION OF THE DRAWINGS

As discussed above, there exists a need to provide a more simplified absorbent article and a more simplified method for constructing absorbent articles. The present invention provides said article and method.

Figure 1:
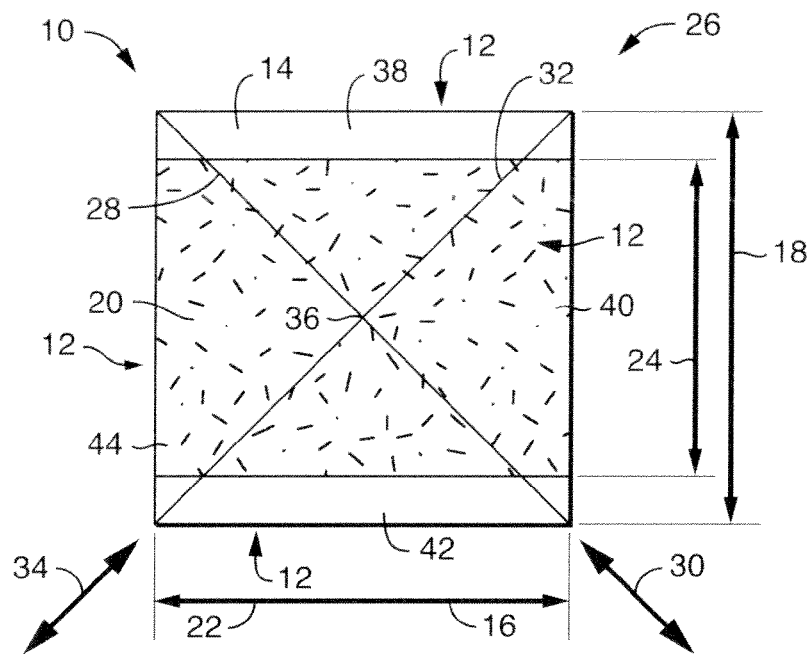
FIG. 1 representatively illustrates an exemplary embodiment of the present invention.

Referring now to FIG. 1, a method 10 for making multiple absorbent articles 12 is illustrated. The method 10 includes the step of providing a rectangular liquid-impermeable layer 14 having a first length 16 and first width 18. The method 10 also includes providing a rectangular absorbent layer 20 having a second length 22 and second width 24. The absorbent layer 20 and the liquid-impermeable layer 14 are joined in facing relation to define an absorbent composite 26.

The method 10 further includes the step of severing the liquid-impermeable layer 14 and the absorbent layer 20 (i.e., severing the absorbent composite 26) at a first cut 28 oriented in a first direction 30, wherein the first direction 30 is non-parallel with the first width 18, the second width 24, the first length 16, or the second length 22.

The method 10 further includes the step of severing the liquid-impermeable layer 14 and the absorbent layer 20 (i.e., severing the absorbent composite 26) at a second cut 32 oriented in a second direction 34, wherein the second direction 34 is non-parallel with the first width 18, the second width 24, the first length 16, or the second length 22. The second cut 32 intersects the first cut 28 at a single junction point 36.

Finally, the method 10 includes the step of separating the composite 26 along the first cut 28 and along the second cut 32 into discrete absorbent articles 12. In some embodiments the method 10 may result in four discrete absorbent articles 12 having a common junction point 36. For example, the method 10 of FIG. 1 illustrates separating the composite 26 to define a first absorbent article 38, a second absorbent article 40, a third absorbent article 42, and a fourth absorbent article 44 all with a common junction point 36. The method 10 of FIG. 1 produces the articles illustrated in FIG. 1A.

Figure 1A:
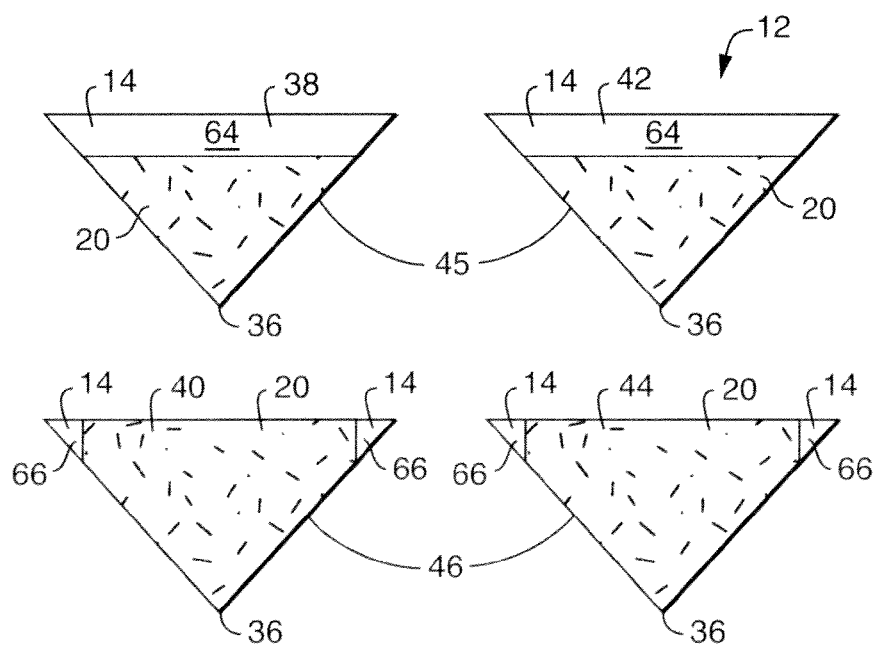
FIG. 1A representatively illustrates exemplary articles resulting from the method of FIG. 1.

In various embodiments, the method 10 may include the step of defining four discrete absorbent articles 12 wherein the four discrete absorbent articles 12 include a first pair of absorbent articles 45 having a first configuration and a second pair of absorbent articles 46 having a second configuration wherein the first configuration and the second configuration are different. For example, as illustrated in FIG. 1A, the first absorbent article 38 and the third absorbent article 42 form the first pair 45 and have the same first configuration. Specifically, the first configuration includes an entire edge 64 wherein the liquid-impermeable layer 14 extends beyond the absorbent layer 20. In contrast, the second absorbent article 40 and the fourth absorbent article 44 form the second pair 46 and have the same second configuration. Specifically, the second configuration includes only two corners 66 wherein the liquid-impermeable layer 14 extends beyond the absorbent layer 20.

In various embodiments, the first configuration of the first pair 45 may have a first absorbent capacity and the second configuration of the second pair 46 may have a second absorbent capacity greater than the first absorbent capacity. For example, in FIG. 1, when the absorbent layer 20 is uniform across the second length 22 and the second width 24, the second configuration of the second absorbent article 40 and the fourth absorbent article 44 have a greater absorbent capacity than the first configuration of the first absorbent article 38 and the third absorbent article 42 because the second configuration includes more of the absorbent layer 20.

In various embodiments, the method 10 may include the step of defining four discrete absorbent articles 12 wherein the four discrete absorbent articles 12 include a first pair of absorbent articles 45 having a first configuration and a second pair of absorbent articles 46 having a second configuration wherein the first configuration and the second configuration are the same. (See e.g., FIG. 3).

In some embodiments, the method 10 may further include the step of cutting holes in the absorbent composites to create leg openings in the resultant absorbent articles 12. For example, referring now to FIG. 2, a method 10 for making multiple absorbent articles 12 is illustrated. The method 10 includes the step of providing a rectangular liquid-impermeable layer 14 having a first length 16 and first width 18. The method 10 also includes providing a rectangular absorbent layer 20 having a second length 22 and second width 24. The absorbent layer 20 and the liquid-impermeable layer 14 are joined in facing relation to define an absorbent composite 26 and an overlap region 47. As used herein, the term "overlap region" describes the area of the absorbent composite that includes both the absorbent layer 20 and the liquid-impermeable layer 14.

The method 10 of this embodiment includes the step of removing a first cut out 48, a second cut out 50, a third cut out 52, and a fourth cut out 54 from the overlap region 47 of the absorbent composite 26 to define a first opening 56, a second opening 58, a third opening 60, and a fourth opening 62.

The method 10 further includes the step of severing the liquid-impermeable layer 14 and the absorbent layer 20 (i.e., severing the absorbent composite 26) at a first cut 28 oriented in a first direction 30, wherein the first direction 30 is non-parallel with the first width 18, the second width 24, the first length 16, or the second length 22. In this embodiment, the first cut 28 severs both the absorbent layer 20 and the liquid-impermeable layer 14 such that the first opening 56 and the third opening 60 span only the first cut 28.

The method 10 further includes the step of severing the liquid-impermeable layer 14 and the absorbent layer 20 (i.e., severing the absorbent composite 26) at a second cut 32 oriented in a second direction 34, wherein the second direction 34 is non-parallel with the first width 18, the second width 24, the first length 16, or the second length 22. The second cut 32 intersects the first cut 28 at a single junction point 36. In this embodiment, the second cut 32 severs both the absorbent layer 20 and the liquid-impermeable layer 14 such that the second opening 58 and the fourth opening 62 span only the second cut 32.

Figure 2:
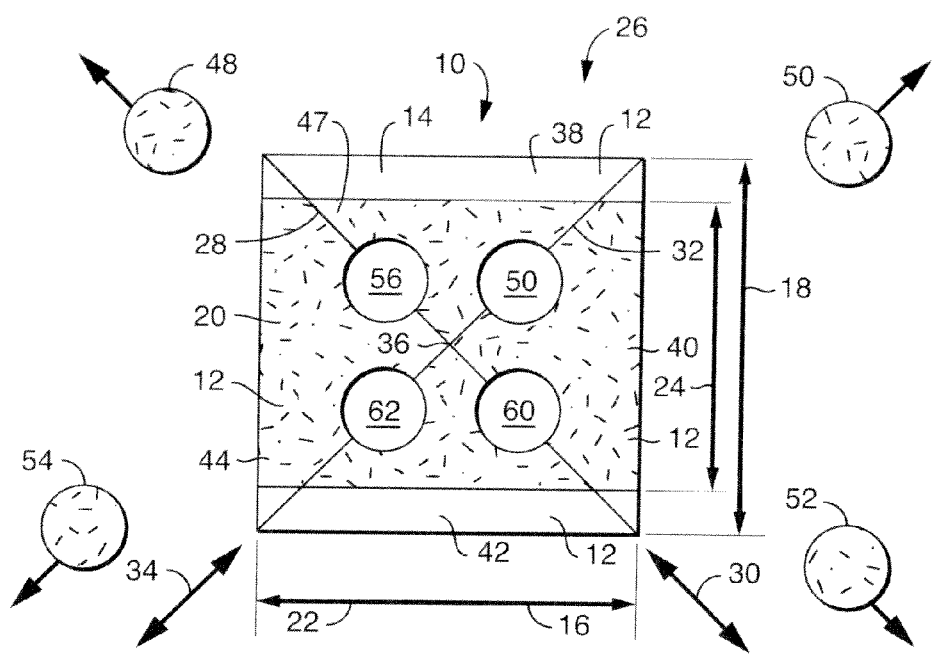
FIG. 2 representatively illustrates an exemplary embodiment of the present invention.

Finally, the method 10 includes the step of separating the absorbent composite 26 along the first cut 28 and the second cut 32 into discrete absorbent articles 12. In some embodiments the method may result in four discrete absorbent articles 12 having a common junction point 36. For example, the method 10 of FIG. 2 illustrates separating the composite 26 to define a first absorbent article 38, a second absorbent article 40, a third absorbent article 42, and a fourth absorbent article 44 all with a common junction point 36. The separated articles of FIG. 2 are illustrated in FIG. 2A.

In various embodiments, the method 10 may also include the step of centering the first opening 56, the second opening 58, the third opening 60, and/or the fourth opening 62 on the first cut 28 and/or the second cut 32. For example, FIG. 2 illustrates the first opening 56 and the third opening 60 being centered on the first cut 28. Likewise, FIG. 2 illustrates the second opening 58 and the fourth opening 62 being centered on the second cut 32.

Figure 2A:
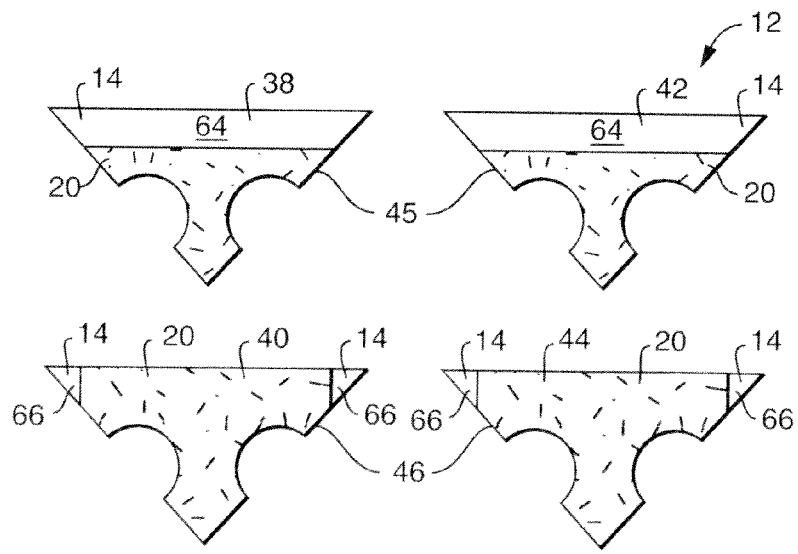
FIG. 2A representatively illustrates exemplary articles resulting from the method of FIG. 2.

In the embodiment of FIGS. 2 and 2A, the method 10 includes the step of defining four discrete absorbent articles 12 wherein the four discrete absorbent articles 12 include a first pair of absorbent articles 45 having a first configuration and a second pair of absorbent articles 46 having a second configuration wherein the first configuration and the second configuration are different. Specifically, the first absorbent article 38 and the third absorbent article 42 form the first pair 45 and have the same first configuration. The first configuration includes an entire edge 64 wherein the liquid-impermeable layer 14 extends beyond the absorbent layer 20. In contrast, the second absorbent article 40 and the fourth absorbent article 44 form the second pair 46 and have the same second configuration. The second configuration includes only two corners 66 wherein the liquid-impermeable layer 14 extends beyond the absorbent layer 20.

When the absorbent layer 20 is uniform across the second length 22 and the second width 24, the second configuration of the second absorbent article 40 and the fourth absorbent article 44 has a greater absorbent capacity than the first configuration of the first absorbent article 38 and the third absorbent article 42 because the second configuration includes more of the absorbent layer 20.

Figure 3:
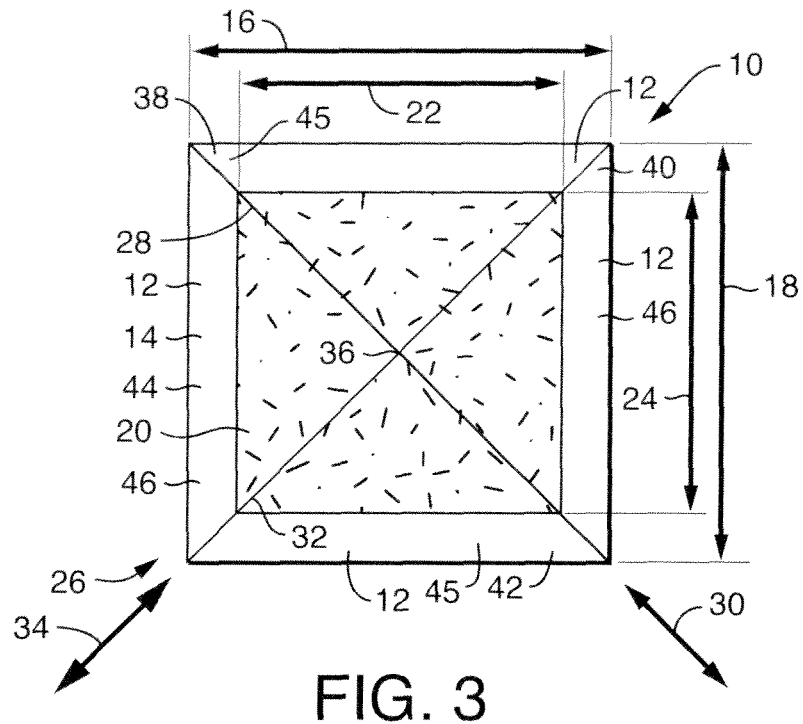
FIGS. 3-10 representatively illustrate exemplary embodiments of the present invention.

Referring now to FIG. 3, a method 10 for making multiple absorbent articles 12 is illustrated. The method 10 includes the step of providing a rectangular liquid-impermeable layer 14 having a first length 16 and first width 18. The method 10 also includes providing a rectangular absorbent layer 20 having a second length 22 and second width 24. In this embodiment, the second length 22 is less than the first length 16 and the second width 24 is less than the first width 18. Also in this embodiment, the second length 22 is the same as the second width 24 making the absorbent layer 20 a square. Likewise, the first length 16 is the same as the first width 18. In other words, the liquid-impermeable layer 14 is also a square. The absorbent layer 20 and the liquid-impermeable layer 14 are joined in facing relation to define an absorbent composite 26.

The method 10 further includes the step of severing the liquid-impermeable layer 14 and the absorbent layer 20 (i.e., severing the absorbent composite 26) at a first cut 28 oriented in a first direction 30, wherein the first direction 30 is non-parallel with the first width 18, the second width 24, the first length 16, or the second length 22.

The method 10 further includes the step of severing the liquid-impermeable layer 14 and the absorbent layer 20 (i.e., severing the absorbent composite 26) at a second cut 32 oriented in a second direction 34, wherein the second direction 34 is non-parallel with the first width 18, the second width 24, the first length 16, or the second length 22. The second cut 32 intersects the first cut 28 at a single junction point 36.

Finally, the method 10 includes the step of separating the composite 26 along the first cut 28 and the second cut 32 into discrete absorbent articles 12. In this embodiment the method 10 results in four discrete absorbent articles 12 having a common junction point 36. Specifically, the method 10 of FIG. 3 illustrates separating the composite 26 to define a first absorbent article 38, a second absorbent article 40, a third absorbent article 42, and a fourth absorbent article 44 all with a common junction point 36.

In this embodiment, the method 10 includes the step of defining four discrete absorbent articles 12 wherein the four discrete absorbent articles 12 include a first pair of absorbent articles 45 having a first configuration and a second pair of absorbent articles 46 having a second configuration wherein the first configuration and the second configuration are the same. Also in this embodiment, the first configuration and the second configuration have the same absorbent capacity.

Figure 4:
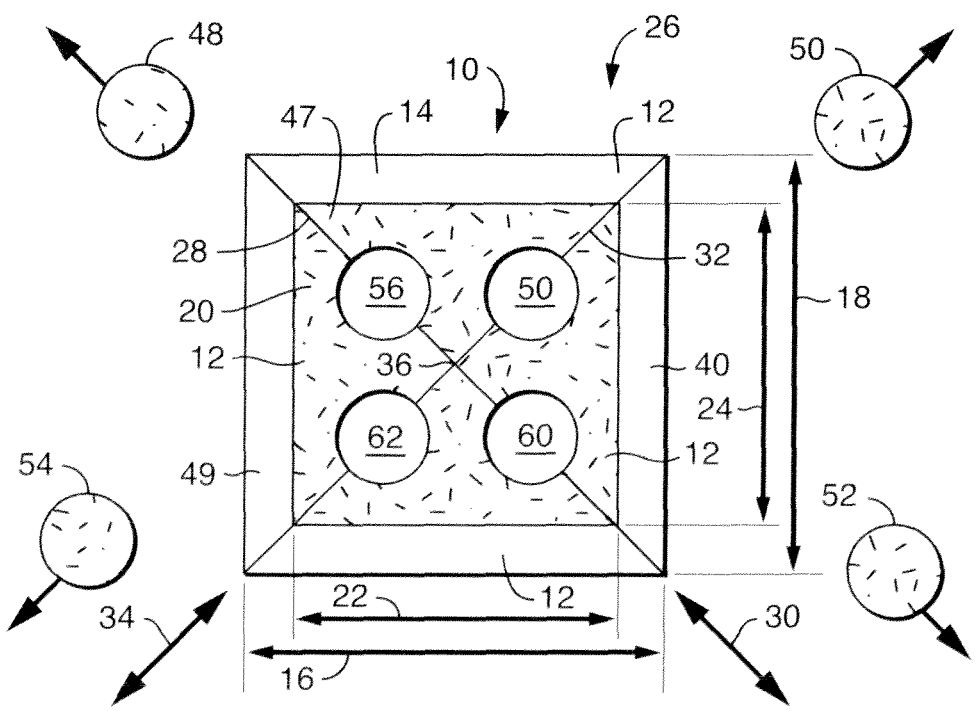

Referring now to FIG. 4, a method 10 for making multiple absorbent articles 12 is illustrated. The method 10 includes the step of providing a rectangular liquid-impermeable layer 14 having a first length 16 and first width 18. The method 10 also includes providing a rectangular absorbent layer 20 having a second length 22 and second width 24. In this embodiment, the second length 22 is less than the first length 16 and the second width 24 is less than the first width 18. Also in this embodiment, the second length 22 is the same as the second width 24 making the absorbent layer 20 a square. Likewise, the first length 16 is the same as the first width 18. In other words, the liquid-impermeable layer 14 is also a square. The absorbent layer 20 and the liquid-impermeable layer 14 are joined in facing relation to define an absorbent composite 26 and an overlap region 47 and an open region 49.

The method 10 of this embodiment includes the step of removing a first cut out 48, a second cut out 50, a third cut out 52, and a fourth cut out 54 from the overlap region 47 of the absorbent composite 26 to define a first opening 56, a second opening 58, a third opening 60, and a fourth opening 62.

The method 10 further includes the step of severing the liquid-impermeable layer 14 and the absorbent layer 20 (i.e., severing the absorbent composite 26) at a first cut 28 oriented in a first direction 30, wherein the first direction 30 is non-parallel with the first width 18, the second width 24, the first length 16, or the second length 22. In this embodiment, the first cut 28 completely severs both the absorbent layer 20 and the liquid-impermeable layer 14 such that the first opening 56 and the third opening 60 span only the first cut 28.

The method 10 further includes the step of severing the liquid-impermeable layer 14 and the absorbent layer 20 (i.e., severing the absorbent composite 26) at a second cut 32 oriented in a second direction 34, wherein the second direction 34 is non-parallel with the first width 18, the second width 24, the first length 16, or the second length 22. The second cut 32 intersects the first cut 28 at a single junction point 36. In this embodiment, the second cut 32 severs both the absorbent layer 20 and the liquid-impermeable layer 14 such that the second opening 58 and the fourth opening 62 span only the second cut 32.

Finally, the method 10 includes the step of separating the absorbent composite 26 along the first cut 28 and the second cut 32 into discrete absorbent articles 12. In some embodiments the method may result in four discrete absorbent articles 12 having a common junction point 36. The method 10 of FIG. 4 illustrates separating the composite 26 to define a first absorbent article 38, a second absorbent article 40, a third absorbent article 42, and a fourth absorbent article 44 all with a common junction point 36.

In various embodiments, the method 10 may also include the step of centering the first opening 56, the second opening 58, the third opening 60, and/or the fourth opening 62 on the first cut 28 and/or the second cut 32. For example, FIG. 4 illustrates the first opening 56 and the third opening 60 being centered on the first cut 28. Likewise, FIG. 4 illustrates the second opening 58 and the fourth opening 62 being centered on the second cut 32. In some embodiments, the method 10 may also include the step of centering the first cut 28 and/or the second cut 32 on the first opening 56, the second opening 58, the third opening 60, and/or the fourth opening 62.

In various embodiments, the first length 16 of the liquid-impermeable layer 14 may be the same or greater than the second length 22 of the absorbent layer 20. Likewise, in various embodiments, the first width 18 of the liquid-impermeable layer 14 may be the same or greater than the second width 24 of the absorbent layer 20. For example, as illustrated in FIGS. 1 and 2, the first length 16 of the liquid-impermeable layer 14 is the same as the second length 22 of the absorbent layer 20 whereas the first width 18 of the liquid-impermeable layer is greater than the second length 22 of the absorbent layer 20. In comparison, FIGS. 3 and 4 illustrate the first length 16 and the first width 18 of the liquid-impermeable layer 14 being greater than the second length 22 and the second width 24 of the absorbent layer 20.

In some embodiments, the second length 22 and/or the second width 24 of the absorbent layer 20 may be centered relative to the first length 16 and/or the first width 18 of the liquid-impermeable layer 14. For example, as illustrated in FIGS. 1-4, the second length 22 and the second width 24 of the absorbent layer 20 are centered relative to the first length 16 and the first width 18 of the liquid-impermeable layer 14.

In various embodiments, the first length 16 and/or the first width 18 of the liquid-impermeable layer 14 may be parallel with the respective second length 22 and/or second width 24 of the absorbent layer 20. For example, as illustrated in FIG. 1-4, the absorbent layer 20 and the liquid-impermeable layer 14 are oriented such that the first length 16 is parallel with the second length 22 and the first width 18 is parallel with the second width 24.

In some embodiments, the first cut 28, the second cut 32, the first cut out 48, the second cut out 40, the third cut out 42, and/or the fourth cut out 44 may only partially sever the absorbent composite 26. For example, in some embodiments, the first cut 28 and/or the second cut 32 may include perforations, scores, or other lines of weakness such that four discrete absorbent articles are defined by the cuts and/or lines of weakness but separation of one or more article from another article requires an additional force to be applied. For example, in one embodiment, the first cut 28 may completely sever the absorbent composite 26 whereas the second cut 32 may produce a line of weakness that is later torn by a user to separate the two attached absorbent articles into discrete absorbent articles. In some embodiments, the first cut 28 and the second cut 32 may both produce lines of weakness adapted to be torn into discrete articles at some future time. In some embodiments, the first cut out 48, the second cut out 40, the third cut out 42, and/or the fourth cut out 44 may only partially sever the absorbent composite 26 and may be separated at some future time.

In various embodiments, the process steps of severing may be performed by any suitable means. For example, the severing steps may be accomplished with a die cutter and press, a rotary cutter, or any other suitable means for cutting and separating one material from another. Likewise, the method steps of the present invention may be undertaken in any suitable sequence. For example, the first cut 28, the second cut 32, the first cut out 48, the second cut out 40, the third cut out 42, and/or the fourth cut out 44 may occur sequentially in any suitable order or may occur essentially simultaneously using any suitable means. Additionally, the step of removing the cut outs may be accomplished using any suitable means such as die cutters, water cutters, laser cutters, pickers, scissors, and the like, and combinations thereof.

In some embodiments, the present invention may provide a method for making multiple absorbent articles involving moving webs and a continuous or semi-continuous process. For example, referring to FIG. 5, a method for making multiple absorbent articles is illustrated generally at 100. The method 100 includes the steps of moving a web of absorbent composite material 102 in a machine direction 104. The absorbent composite material 102 includes a liquid-impermeable layer 106 joined in facing relation with an absorbent material layer 108 to define an overlap region 110.

Figure 5:
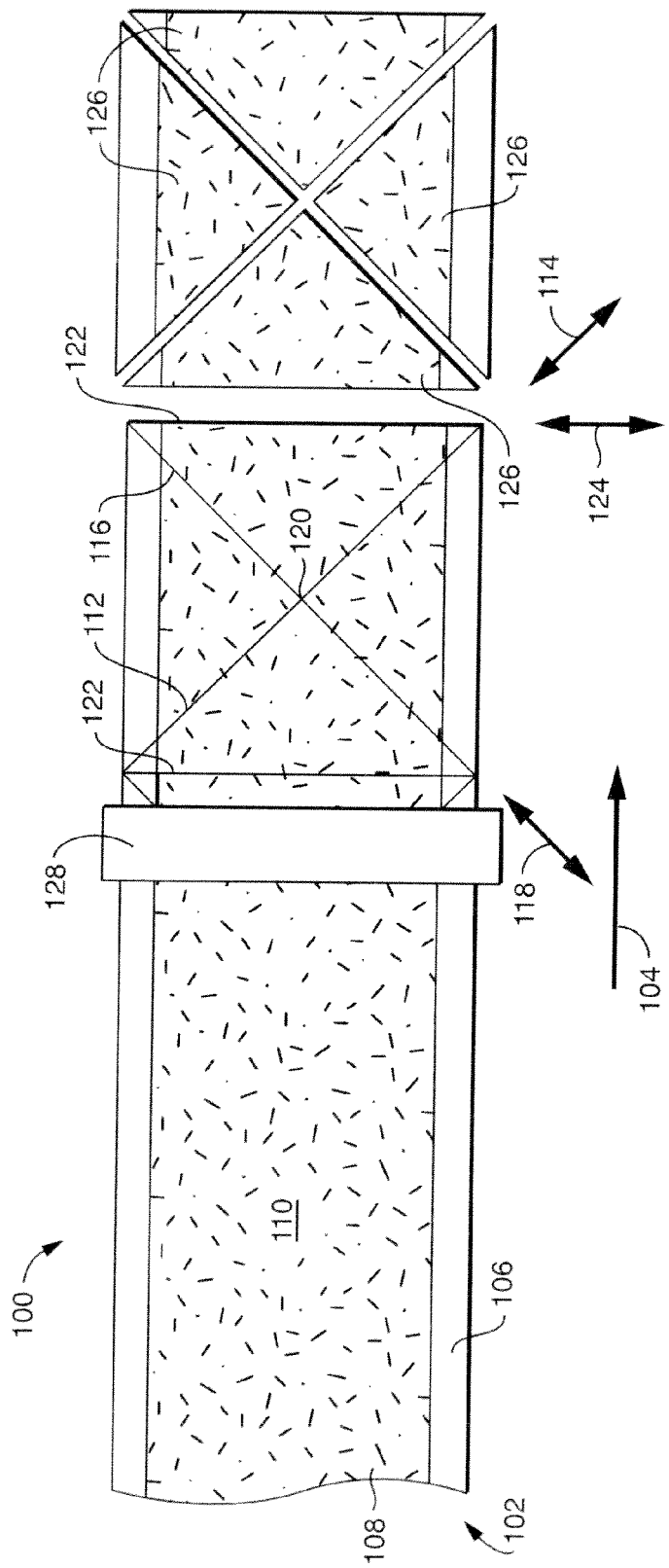

The method 100 further includes the step of severing the absorbent composite material 102 (liquid-impermeable layer 106 and the absorbent layer 108) at a first cut 112 oriented in a first direction 114, wherein the first direction 114 is non-parallel and non-perpendicular with the machine direction 104. The method 100 further includes the step of severing the absorbent composite material 102 (liquid-impermeable layer 106 and the absorbent layer 108) at a second cut 116 oriented in a second direction 118. The second direction 118 is non-parallel and non-perpendicular with the machine direction 104. Additionally, the second cut 116 intersects the first cut 112 at an intersection 120. The method 100 further includes the step of severing the absorbent composite 102 at a third cut 122 oriented in a third direction 124. The third direction 124 is perpendicular or substantially perpendicular to the machine direction 104. As illustrated in FIG. 5, all severing steps are illustrated collectively at 128.

After cutting the absorbent composite material 102, the method 100 further includes the step of separating the absorbent composite material 102 at the first cut 112, the second cut 116, and the third cut 122 into discrete absorbent articles 126.

Figure 6:
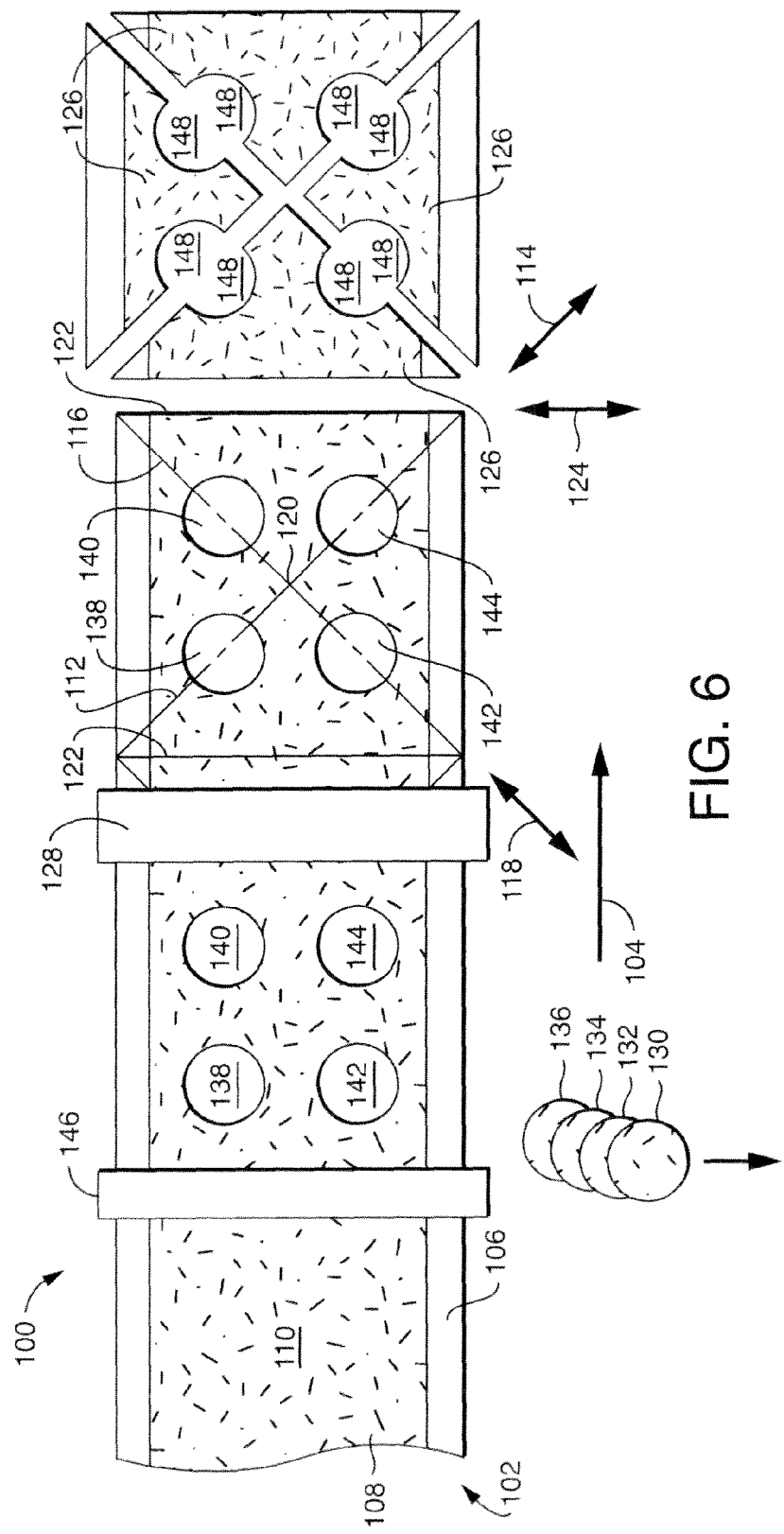

In some embodiments, the method may further include steps for creating leg cut outs as illustrated in FIG. 6. Referring to FIG. 6, a method for making multiple absorbent articles is illustrated generally at 100. The method 100 includes the steps of moving a web of absorbent composite material 102 in a machine direction 104. The absorbent composite material 102 includes a liquid-impermeable layer 106 joined in facing relation with an absorbent material layer 108 to define an overlap region 110.

The method 100 further includes the step of removing a first cut out 130, a second cut out 132, a third cut out 134, and a fourth cut out 136 from the overlap region 110 of the absorbent composite 102 to define a first opening 138, a second opening 140, a third opening 142, and a fourth opening 144. As illustrated, all cut out steps are illustrated collectively at 146.

The method 100 further includes the step of severing the absorbent composite material 102 (liquid-impermeable layer 106 and the absorbent layer 108) at a first cut 112 oriented in a first direction 114, wherein the first direction 114 is non-parallel and non-perpendicular with the machine direction 104 and spans only two of the first opening 138, the second opening 140, the third opening 142, and the fourth opening 144. For example, as illustrated in FIG. 6, the first cut 112 spans only the first opening 138 and the fourth opening 144 but does not span the second opening 140 or the third opening 142.

The method 100 further includes the step of severing the absorbent composite material 102 (liquid-impermeable layer 106 and the absorbent layer 108) at a second cut 116 oriented in a second direction 118. The second direction 118 is non-parallel and non-perpendicular with the machine direction 104. Additionally, the second cut 116 intersects the first cut 112 at an intersection 120 and spans only two of the first opening 138, the second opening 140, the third opening 142, and the fourth opening 144. For example, as illustrated in FIG. 6, the second cut 116 spans only the second opening 140 and the third opening 142 but does not span the first opening 138 or the fourth opening 144.

The method 100 further includes the step of severing the absorbent composite 102 at a third cut 122 oriented in a third direction 124. The third direction 124 is perpendicular or substantially perpendicular to the machine direction 104. As illustrated, all severing steps are illustrated collectively at 128.

After cutting the absorbent composite material 102, the method 100 further includes the step of separating the absorbent composite material 102 at the first cut 112, the second cut 116, and the third cut 122 into discrete absorbent articles 126 having leg openings 148.

In some embodiments, the present invention may provide a method for making multiple absorbent articles involving discrete absorbent material layers. For example, referring to FIG. 7, a method for making multiple absorbent articles is illustrated generally at 100. The method 100 includes the steps of moving a web of absorbent composite material 102 in a machine direction 104. The absorbent composite material 102 includes a liquid-impermeable layer 106 joined in facing relation with discrete absorbent material pieces 149 to define an overlap region 110 and open regions 150.

The method 100 further includes the step of severing the absorbent composite material 102 (liquid-impermeable layer 106 and the discrete absorbent material pieces 149) at a first cut 112 oriented in a first direction 114, wherein the first direction 114 is non-parallel and non-perpendicular with the machine direction 104. The method 100 further includes the step of severing the absorbent composite material 102 (liquid-impermeable layer 106 and the discrete absorbent material pieces 149) at a second cut 116 oriented in a second direction 118. The second direction 118 is non-parallel and non-perpendicular with the machine direction 104. Additionally, the second cut 116 intersects the first cut 112 at an intersection 120. The method 100 further includes the step of severing the absorbent composite 102 at a third cut 122 oriented in a third direction 124. The third direction 124 is perpendicular or substantially perpendicular to the machine direction 104. The third cut 122 severs the absorbent composite material 102 in the open region 150. All severing steps are illustrated collectively at 128.

After cutting the absorbent composite material 102, the method 100 further includes the step of separating the absorbent composite material 102 at the first cut 112, the second cut 116, and the third cut 122 into discrete absorbent articles 126.

Figure 8:
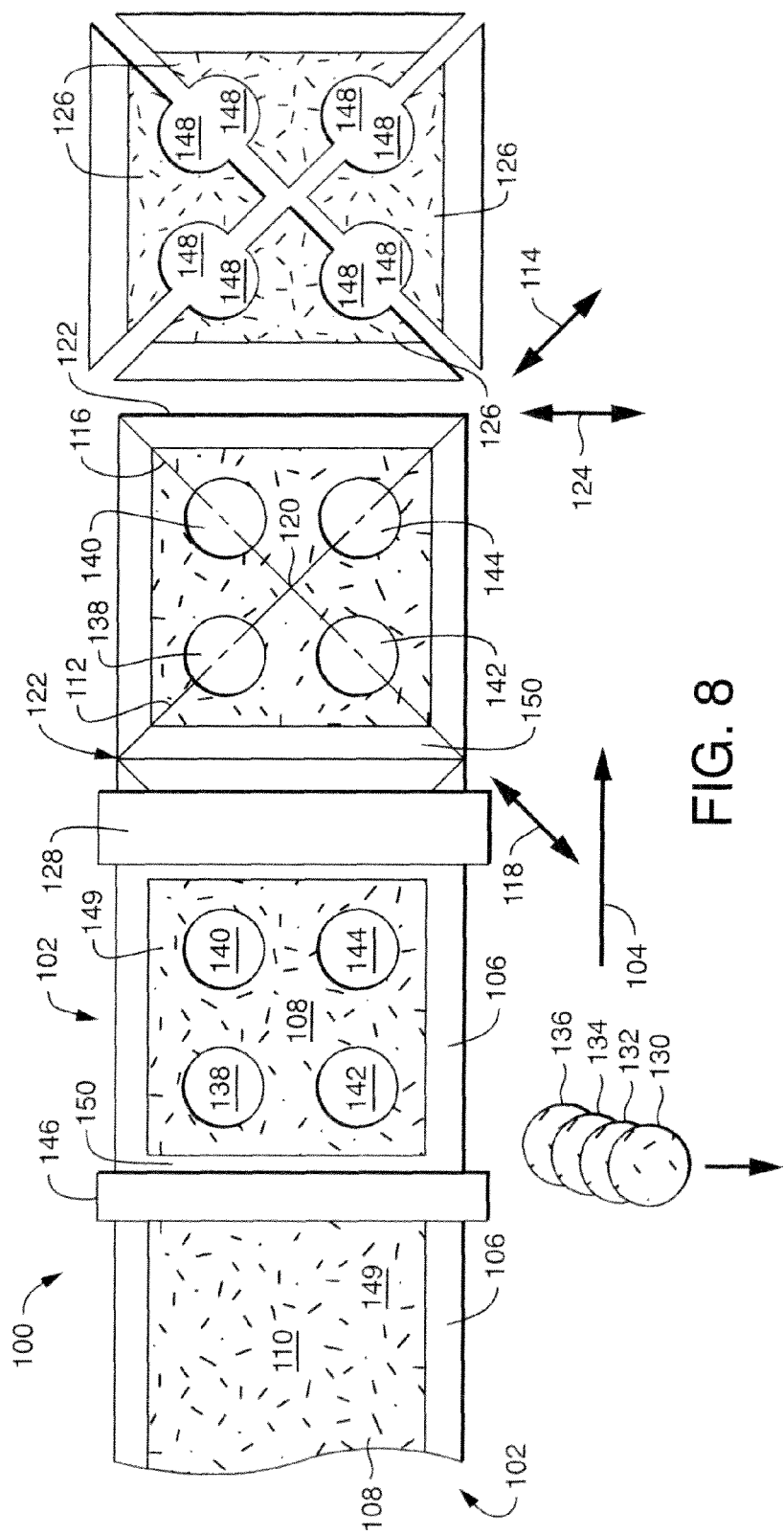

In some embodiments, the method may further include steps for creating leg cut outs in discrete absorbent pieces as illustrated in FIG. 8. Referring to FIG. 8, a method for making multiple absorbent articles is illustrated generally at 100. The method 100 includes the steps of moving a web of absorbent composite material 102 in a machine direction 104. The absorbent composite material 102 includes a liquid-impermeable layer 106 joined in facing relation with discrete absorbent material pieces 149 to define an overlap region 110 and open regions 150.

The method 100 further includes the step of removing a first cut out 130, a second cut out 132, a third cut out 134, and a fourth cut out 136 from the overlap region 110 of the absorbent composite 102 to define a first opening 138, a second opening 140, a third opening 142, and a fourth opening 144. All cut out steps are illustrated collectively at 146.

The method 100 further includes the step of severing the absorbent composite material 102 (liquid-impermeable layer 106 and the absorbent layer 108) at a first cut 112 oriented in a first direction 114, wherein the first direction 114 is non-parallel and non-perpendicular with the machine direction 104 and spans only two of the first opening 138, the second opening 140, the third opening 142, and the fourth opening 144. For example, as illustrated in FIG. 6, the first cut 112 spans only the first opening 138 and the fourth opening 144 but does not span the second opening 140 or the third opening 142.

The method 100 further includes the step of severing the absorbent composite material 102 (liquid-impermeable layer 106 and the absorbent layer 108) at a second cut 116 oriented in a second direction 118. The second direction 118 is non-parallel and non-perpendicular with the machine direction 104. Additionally, the second cut 116 intersects the first cut 112 at an intersection 120 and spans only two of the first opening 138, the second opening 140, the third opening 142, and the fourth opening 144. For example, as illustrated in FIG. 6, the second cut 116 spans only the second opening 140 and the third opening 142 but does not span the first opening 138 or the fourth opening 144.

The method 100 further includes the step of severing the absorbent composite 102 at a third cut 122 oriented in a third direction 124. The third direction 124 is perpendicular or substantially perpendicular to the machine direction 104. The third cut 122 severs the absorbent composite material 102 in the open region 150. All severing steps are illustrated collectively at 128.

After cutting the absorbent composite material 102, the method 100 further includes the step of separating the absorbent composite material 102 at the first cut 112, the second cut 116, and the third cut 122 into discrete absorbent articles 126 having leg openings 148.

In various embodiments, the cutting steps may occur sequentially or concurrently in various embodiments. Likewise, the first cut 112, the second cut 116, and/or the third cut 122 may be executed in a single cutting unit or two or more cutting units. Additionally, the first cut 112, the second cut 116, and/or the third cut 122 may be executed via any suitable cutting device or devices such as, for example, die cutters, water cutters, slitters, laser cutters, or the like, or combinations thereof. For example, in one embodiment, the first cut 112 and the second cut 116 may be produced with a rotary knife and anvil apparatus in a first operation and the third cut 122 may be produced by a rotary knife and anvil apparatus in a second operation. For sake of illustration, the cutting apparatus necessary for the first cut 112, the second cut 116, and the third cut 122 is collectively represented generally at 128.

In some embodiments, a rotary knife and anvil may be used to sever the absorbent composite material 102 at the first cut 112, the second cut 116, and the third cut 122 using the same cutting apparatus. In these embodiments, the cuts are considered to be made contemporaneously.

In some embodiments, a first knife roll may be used to sever the absorbent composite 102 at the first cut 112, a second knife roll may be used to sever the absorbent composite 102 at the second cut 116, and a third knife roll is used to sever the absorbent composite 102 at the third cut 122. In these embodiments, the cuts are considered to be made sequentially.

In some embodiments, the first cut 112, the second cut 116, the third cut 122, the first cut out 130, the second cut out 132, the third cut out 134, and/or the fourth cut out 136, and/or combinations thereof may only partially sever or otherwise weaken the absorbent composite 102. For example, in some embodiments, the first cut 112 and/or the second cut 116 and/or the third cut 122 may include perforations, scores, or other lines of weakness such that discrete absorbent articles 126 are defined by the cuts and/or lines of weakness but separation of any one or more discrete absorbent articles 126 from another absorbent article 126 requires an additional force to be applied. For example, in one embodiment, the first cut 112 may completely sever the absorbent composite 102 and the third cut 122 may completely sever the absorbent composite 102 whereas the second cut 116 may produce a line of weakness that is later torn by a user to separate the two attached absorbent articles into discrete absorbent articles 126. In some embodiments, the third cut 122 may completely sever the absorbent composite 102 whereas the first cut 112 and the second cut 116 may produce lines of weakness adapted to be torn into discrete articles at some future time. In other words, the absorbent composite 102 may be cut into sub-units wherein each sub-unit includes four discrete absorbent articles 126 attached together via lines of weakness. The lines of weakness may be broken at some later time to separate the discrete absorbent articles 126.

In various embodiments involving leg cut outs, the creation of the first cut out 130, the second cut out 132, the third cut out 134, and/or the fourth cut out 136 may occur sequentially or concurrently in various embodiments. In some embodiments, the creation of the first cut out 130, the second cut out 132, the third cut out 134, and/or the fourth cut out 136 may occur before, after, or concurrently with the first cut 112, the second cut 116, and/or the third cut 122. Likewise, the first cut out 130, the second cut out 132, the third cut out 134, and/or the fourth cut out 136 may be executed via a single cutting unit or two or more cutting units. Additionally, the first cut out 130, the second cut out 132, the third cut out 134, and/or the fourth cut out 136 may be executed via any suitable cutting device or devices such as, for example, die cutters, water cutters, slitters, laser cutters, or the like, or combinations thereof. For example, in one embodiment, the first cut out 130, the second cut out 132, the third cut out 134, and the fourth cut out 136 may be produced with a rotary knife and anvil apparatus in a single operation. For sake of illustration, the cutting apparatus necessary for the first cut out 130, the second cut out 132, the third cut out 134, and the fourth cut out 136 is collectively represented at 146.

In various embodiments, the first cut out 130, the second cut out 132, the third cut out 134, and/or the fourth cut out 136 may be any suitable shape and any suitable size. For example, the cut outs may be generally circular or oval as illustrated herein.

In the various embodiments described herein, the liquid-impermeable layer may be any suitable material or combination of materials. The liquid-impermeable layer may comprise a single layer of liquid impermeable material or may comprise a multi-layered laminate structure in which at least one of the layers is liquid impermeable. While it is not a necessity for the outer layer of the laminate structure to be liquid permeable, it is suitable that it provides a relatively cloth-like texture to the wearer. Alternatively, the liquid-impermeable layer may comprise a film or may comprise a woven or nonwoven fibrous web layer that has been totally or partially constructed or treated to impart the desired levels of liquid impermeability to selected regions that are adjacent or proximate the absorbent structure. The liquid-impermeable layer may also be stretchable, and in some embodiments it may be elastomeric. Reference is made to U.S. Pat. No. 5,883, 028, issued to Morman et al., U.S. Pat. No. 5,116,662 issued to Morman and U.S. Pat. No. 5,114,781 issued to Morman, all of which are hereby incorporated herein by reference, for additional information regarding suitable liquid-impermeable layers.

In the various embodiments described herein, the absorbent layer may be any suitable material or combination of materials. For example, in some embodiments, the absorbent layer may be compressible, conformable, non-irritating to a wearer's skin, and capable of absorbing and retaining liquids and certain body wastes. For example, the absorbent layer may comprise cellulosic fibers (e.g., wood pulp fibers), other natural fibers, synthetic fibers, woven or nonwoven sheets, foams, scrim netting or other stabilizing structures, superabsorbent material, binder materials, surfactants, selected hydrophobic materials, pigments, lotions, odor control agents, or the like, as well as combinations thereof.

The absorbent layer may be formed into an absorbent web structure by employing various conventional methods and techniques known in the art. For example, the absorbent layer may be formed by a dry-forming technique, an air-forming technique, a wet-forming technique, a foam-forming technique, or the like, as well as combinations thereof. The absorbent layer may alternatively comprise a coform material such as the material disclosed in U.S. Pat. No. 4,100,324 to Anderson, et al. Superabsorbent material may be in the absorbent layer in an amount of from about 0 to about 90 weight percent based on total weight of the absorbent layer. Superabsorbent materials are well known in the art and can be selected from natural, synthetic, and modified natural polymers and materials.

In various embodiments, the absorbent layer may include a single stratum of absorbent material. In other embodiments, the absorbent layer may include two or more strata of absorbent material. The various strata may be composed of any suitable combination of absorbent materials.

Figure 7:
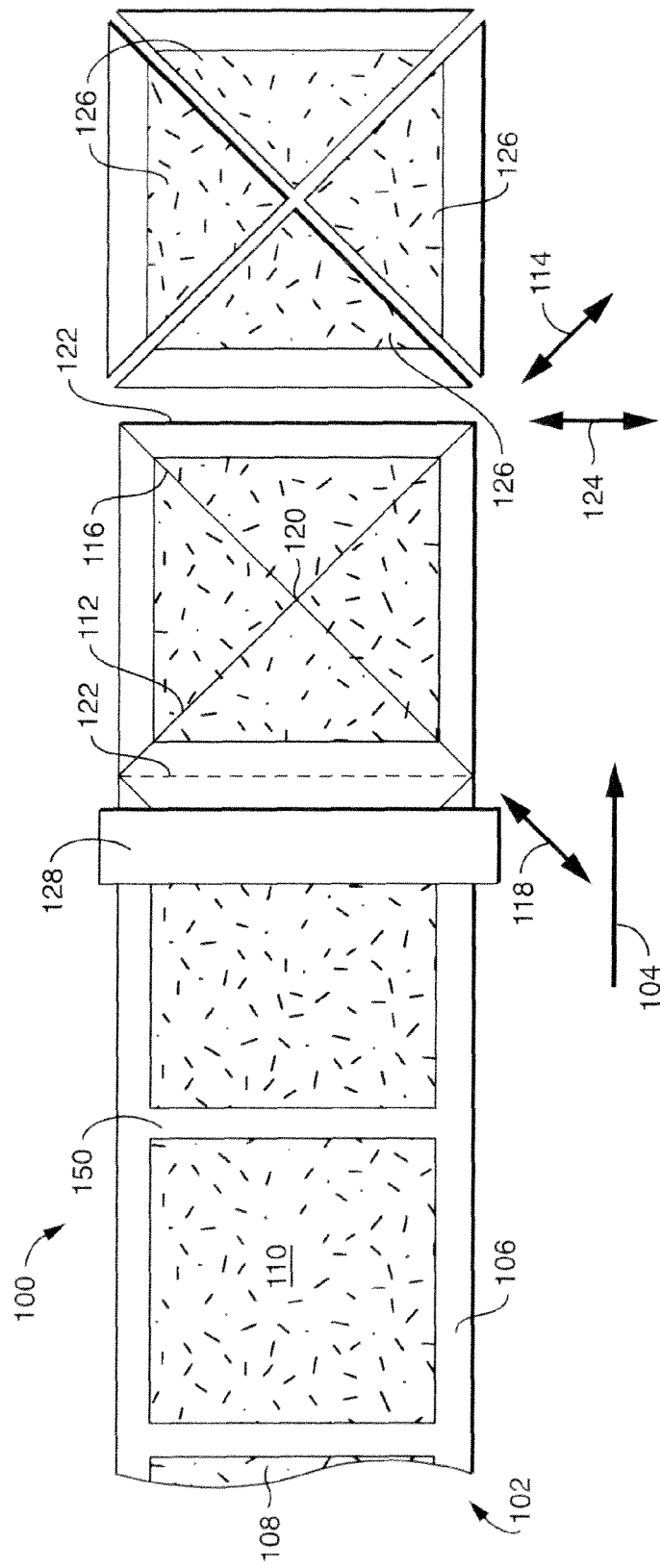

In various embodiments, the absorbent layer may have any suitable shape, size, and orientation. For example, in some embodiments, the absorbent layer 20 may have a rectangular shape as illustrated in FIG. 1. In other embodiments, the absorbent layer 20 may be generally square as illustrated in FIGS. 3, 4, and 7. In some embodiments, the absorbent layer may have a circular shape or any other suitable shape. In some embodiments, the absorbent layer may have a size that is generally the same as the liquid-impermeable layer in length, width, or both. For example, in FIG. 1, the absorbent layer 20 has a length 22 that is equal to the length 16 of the liquid-impermeable layer 14 but a width 24 that is less than the width 18 of the liquid-impermeable layer 14. In some embodiments, the absorbent layer 20 may be oriented relative to the liquid-impermeable layer 14 such that the lengths 16 and 22 are generally parallel and the widths 18 and 24 are generally parallel. In other embodiments, the absorbent layer 20 may be oriented relative to the liquid-impermeable layer 14 such that the length 16 is non-parallel to the length 22 as illustrated in FIG. 9.

Figure 9:
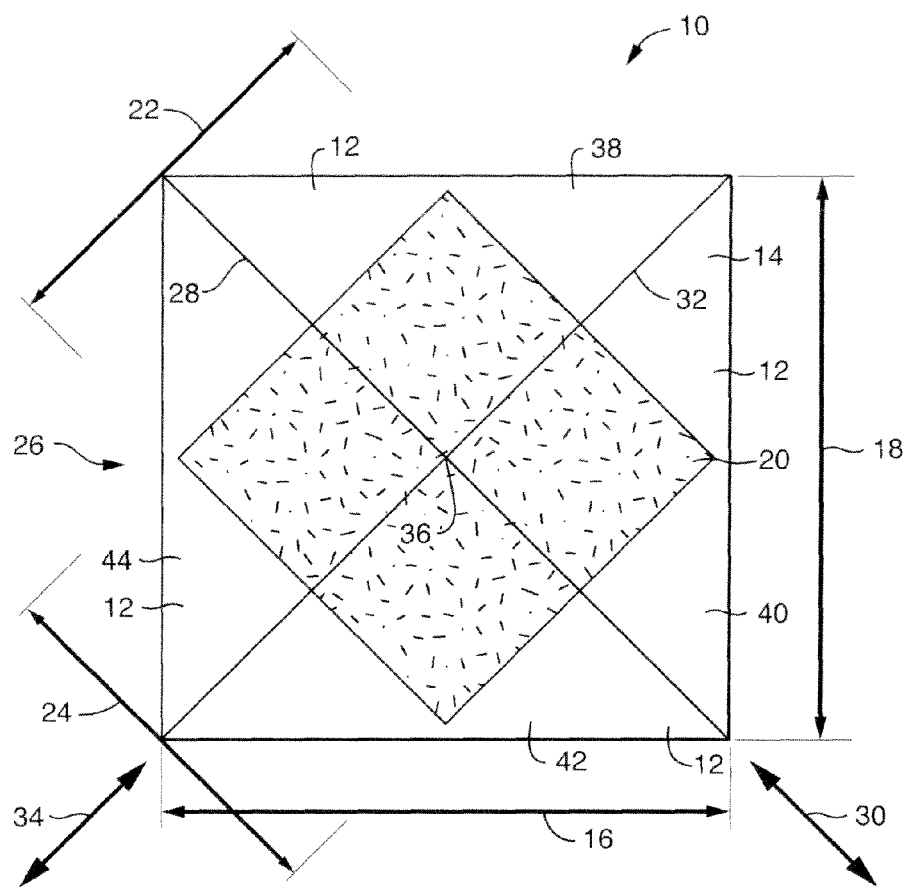

Referring now to FIG. 9, a method 10 for making multiple absorbent articles 12 is illustrated. The method 10 includes the step of providing a rectangular liquid-impermeable layer 14 having a first length 16 and first width 18. The method 10 also includes providing a rectangular absorbent layer 20 having a second length 22 and a second width 24. The absorbent layer 20 and the liquid-impermeable layer 14 are joined in facing relation to define an absorbent composite 26. As illustrated in FIG. 9, the absorbent layer 20 is oriented relative to the liquid-impermeable layer 14 such that the first length 16 is non-parallel with the second length 22 and the first width 18 is non-parallel with the second width 24.

The method 10 further includes the step of severing the liquid-impermeable layer 14 and the absorbent layer 20 (i.e., severing the absorbent composite 26) at a first cut 28 oriented in a first direction 30, wherein the first direction 30 is non-parallel with the first width 18 or the first length 16. The method 10 further includes the step of severing the liquid-impermeable layer 14 and the absorbent layer 20 (i.e., severing the absorbent composite 26) at a second cut 32 oriented in a second direction 34, wherein the second direction 34 is non-parallel with the first width 18 or the first length 16. The second cut 32 intersects the first cut 28 at a single junction point 36.

Figure 9A:
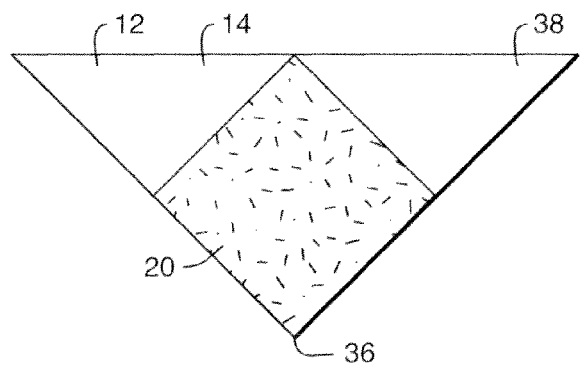
FIG. 9A representatively illustrates an exemplary article resulting from the method of FIG. 9.

Finally, the method 10 includes the step of separating the composite 26 along the first cut 28 and along the second cut 32 into discrete absorbent articles 12. In some embodiments the method 10 may result in four discrete absorbent articles 12 having a common junction point 36. For example, the method 10 of FIG. 9 illustrates separating the composite 26 to define a first absorbent article 38, a second absorbent article 40, a third absorbent article 42, and a fourth absorbent article 44 all with a common junction point 36. The method 10 of FIG. 9 produces four identical articles, one of which is illustrated in FIG. 9A.

Figure 10:
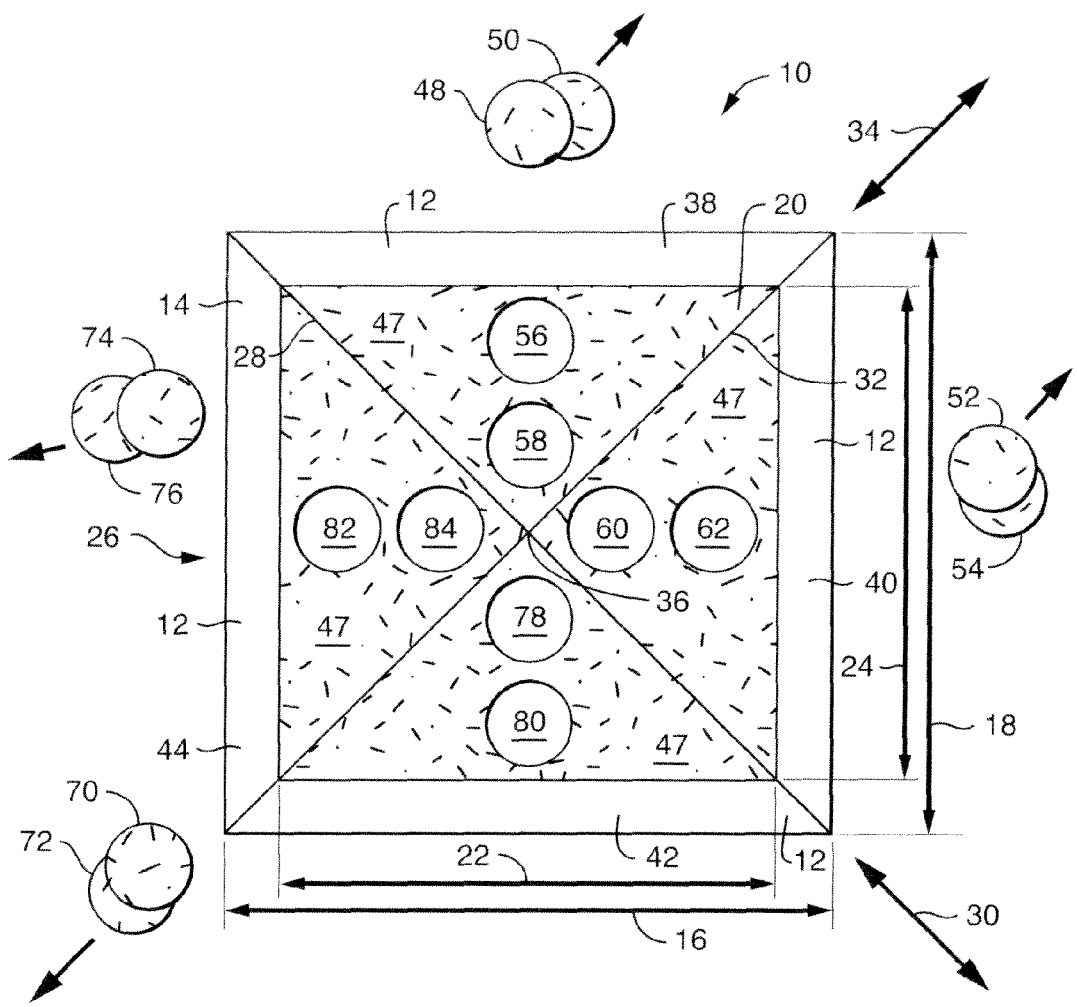
Figure 10A:
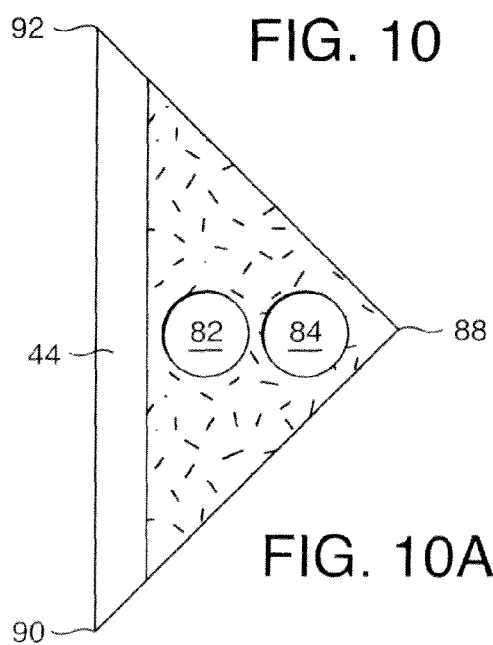
FIG. 10A representatively illustrates an exemplary article resulting from the method of FIG. 10.

In some embodiments, the leg cut outs may be completely contained within the individual absorbent articles. For example, referring now to FIG. 10, a method 10 for making multiple absorbent articles 12 is illustrated. The method 10 includes the step of providing a rectangular liquid-impermeable layer 14 having a first length 16 and first width 18. The method 10 also includes providing a rectangular absorbent layer 20 having a second length 22 and a second width 24. The absorbent layer 20 and the liquid-impermeable layer 14 are joined in facing relation to define an absorbent composite 26. As illustrated in FIG. 10, the absorbent layer 20 is oriented relative to the liquid-impermeable layer 14 such that the first length 16 is parallel with the second length 22 and the first width 18 is parallel with the second width 24.

The method 10 of this embodiment includes the step of removing a first cut out 48, a second cut out 50, a third cut out 52, a fourth cut out 54, a fifth cut out 70, a sixth cut out 72, a seventh cut out 74, and an eighth cut out 76 from the overlap region 47 of the absorbent composite 26 to define a first opening 56, a second opening 58, a third opening 60, a fourth opening 62, a fifth opening 78, a sixth opening 80, a seventh opening 82, and an eighth opening 84.

The method 10 further includes the step of severing the liquid-impermeable layer 14 and the absorbent layer 20 (i.e., severing the absorbent composite 26) at a first cut 28 oriented in a first direction 30, wherein the first direction 30 is non-parallel with the first width 18, the second width 24, the first length 16, or the second length 22. The method 10 further includes the step of severing the liquid-impermeable layer 14 and the absorbent layer 20 (i.e., severing the absorbent composite 26) at a second cut 32 oriented in a second direction 34, wherein the second direction 34 is non-parallel with the first width 18, the second width 24, the first length 16, or the second length 22. The second cut 32 intersects the first cut 28 at a single junction point 36.

Finally, the method 10 includes the step of separating the composite 26 along the first cut 28 and along the second cut 32 to define a first absorbent article 38, a second absorbent article 40, a third absorbent article 42, and a fourth absorbent article 44 all with a common junction point 36. In this embodiment, the first cut 28 and the second cut 32 sever both the absorbent layer 20 and the liquid-impermeable layer 14 such that the first opening 56 and the second opening 58 are completely within the first absorbent article 38, the third opening 60 and the fourth opening 62 are completely within the second absorbent article 40, the fifth opening 78 and the sixth opening 80 are completely within the third absorbent article 42, the seventh opening 82 and the eighth opening 84 are completely within the fourth absorbent article 44.

The method 10 of FIG. 10 produces four identical articles, one of which is illustrated as 44 in FIG. 1A. The article 44 includes leg openings 82 and 84 that are adapted to receive a wearer's legs. In use, a first corner 88 is oriented toward the wearer's hip. A second corner 90 and a third corner 92 are adapted to wrap around the wearer's front and back waist areas and be secured to each other and/or the first corner 88 at the wearer's hip. The corners 88, 90, and 92 may be secured together by any suitable means. For example, the second corner 90 and the third corner 92 may be tied together to create a connection and the first corner 88 may be tucked, folded, or otherwise secured to the connection.

In various embodiments, the methods described herein may also include additional steps for adding other optional components to the discrete absorbent articles. For example, in some embodiments, the methods may also include the steps for adding a bodyside liner layer, a surge layer, containment flaps, elastics, fasteners, loops, belts, lotions, or other conventional components, or combinations thereof.

The methods described herein may also include various means for providing the discrete absorbent articles to retailers and/or consumers. For example, the discrete absorbent articles may be provided in a continuous web wherein the articles are connected by lines of weakness. In such embodiments, the retailer and/or consumer may separate one absorbent article from the remaining articles by breaking the line of weakness. For example, the absorbent articles may be connected by perforations wherein the perforations are torn to separate the discrete article. In some embodiments, the discrete absorbent article may be provided with the cut outs still attached via a line of weakness. In these embodiments, the retailer and/or consumer may separate the cut out from the absorbent article by breaking the line of weakness. In various embodiments, the removed cut out may be used as an auxiliary absorbent device like a wipe.

In some embodiments, the discrete absorbent articles may be provided to retailers and/or consumers in pairs wherein the absorbent articles comprising each pair are attached together along a line of weakness. The line of weakness can be broken to separate the absorbent articles. In some embodiments, a first pair of absorbent articles may have a different configuration than a second pair. In some embodiments, one or more pairs of absorbent articles may include a first absorbent article and a second absorbent article having different configurations.

Figure 11:
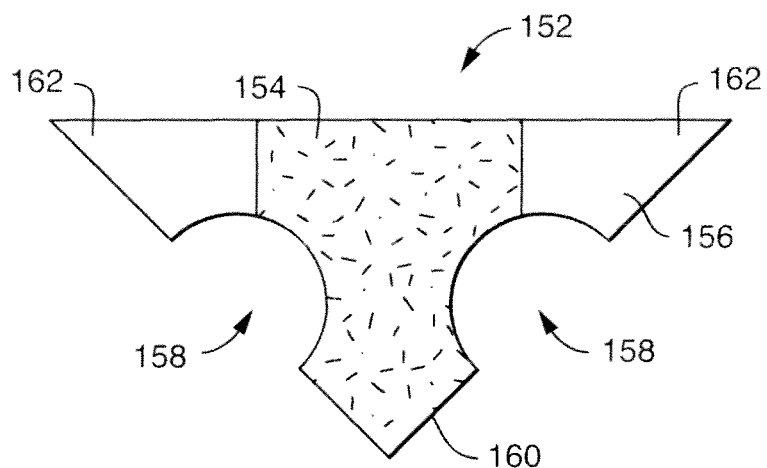
FIG. 11 representatively illustrates an exemplary article produced by the methods of the present invention.
Figure 12:
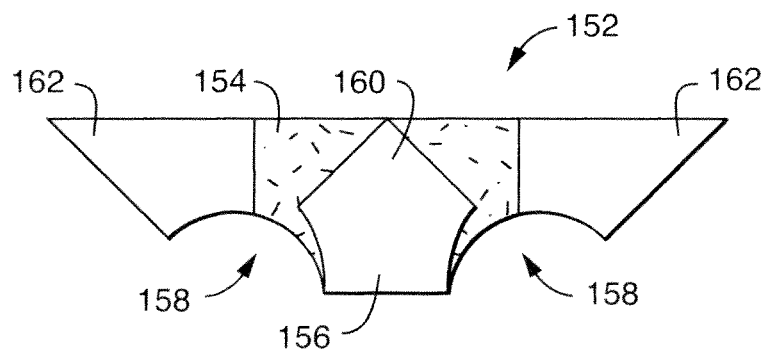
FIG. 12 representatively illustrates the article of FIG. 11 in a partially folded condition.
Figure 13:
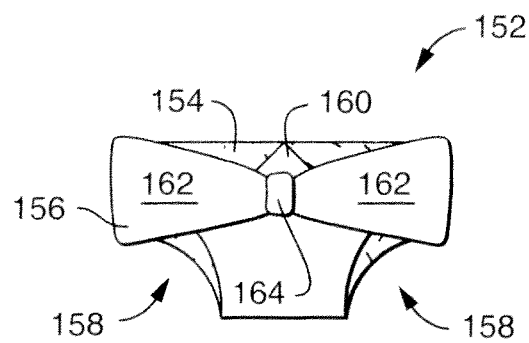
FIG. 13 representatively illustrates the article of FIG. 11 in a fully folded condition.

The absorbent articles produced by the methods described herein may be generally triangular in shape as representatively illustrated in FIG. 11. The article 152 of FIG. 11 is illustrated with the absorbent portion 154 facing the viewer. The absorbent portion 154 overlies the liquid-impermeable backsheet 156 and may be joined thereto. The article 152 may include leg cut outs 158 as illustrated in FIG. 11. In use, the article 152 is laid as illustrated in FIG. 11 and a user (e.g., an infant) is positioned on their back on the article 152 with their legs aligned with the leg cut outs 158. The front portion 160 of the article 152 is pulled up between the legs to the position illustrated in FIG. 12. Finally, the side portions 162 of the article 152 are overlapped across the stomach of the user to the position illustrated in FIG. 13. The front portion 160 and the side portions 162 may be secured in any suitable manner at connection 164 to maintain the absorbent article in position on the wearer.

Connection 164 may be any suitable arrangement. For example, the side portions 162 may be tied together at connection 164 over the front portion 160 to maintain the front portion in position. In the illustrated embodiment, the liquid-impermeable backsheet extends beyond the absorbent in the side portions 162 to provide a suitable location for tying. In another example, the connection 164 may include any suitable mechanical connector or connectors. For example, the connection 164 may include a clip, clamp, or other suitable grasping device. Likewise, the connection 164 may include adhesives, cohesives, magnets, hooks and loops, hoops, clips, clamps, snaps, pockets, straps, and the like, and combinations thereof.

In various embodiments, the various connectors may be integral with the article or may be provided as a separate component. In some embodiments, the connectors may be a combination of integral components and separate components. For example, the absorbent article 152 may include loop material in the front portion 160, side portions 162 or both and a separate piece of hook material may be provided to work in cooperation with the loop material to create connection 164.

While the invention has been described in detail with respect to specific embodiments thereof, it will be appreciated that those skilled in the art, upon attaining understanding of the foregoing will readily appreciate alterations to, variations of, and equivalents to these embodiments. Accordingly, the scope of the present invention should be assessed as that of the appended claims and any equivalents thereto. Additionally, all combinations and/or sub-combinations of the disclosed embodiments, ranges, examples, and alternatives are also contemplated.

The invention claimed is:

1. A method for making multiple absorbent articles comprising,
providing a rectangular liquid-impermeable layer having a first length and a first width,
providing an absorbent layer having a second length and a second width,
joining the absorbent layer and the liquid-impermeable layer in facing relation to define an absorbent composite,
severing the absorbent composite at a first cut oriented in a first direction, the first cut at least partially severing the absorbent layer, wherein the first direction is non-parallel with the first width or the first length, and
severing the absorbent composite at a second cut oriented in a second direction, the second cut at least partially severing the absorbent layer, wherein the second direction is non-parallel with the first width or the first length, wherein the second cut intersects the first cut, and wherein the absorbent composite is severed at the first cut and the second cut to define a plurality of discrete absorbent articles each having at least one of side portions or corners, the at least one of side portions or corners being adapted to be secured together to maintain the plurality of discrete absorbent articles on a wearer.

2. The method of claim 1 wherein the absorbent composite is completely severed by the first cut and the second cut to define four discrete absorbent articles having a common junction point.

3. The method of claim 1 wherein the first length is equal to the second length and the first width is greater than second width.

4. The method of claim 3 wherein the absorbent layer is centered relative to the liquid-impermeable layer.

5. The method of claim 1 wherein the first length is greater than the second length and the first width is greater than the second width and the absorbent layer is centered relative to the liquid-impermeable layer.

6. The method of claim 2 wherein the four discrete absorbent articles comprise a first pair of absorbent articles having a first configuration and a second pair of absorbent articles having a second configuration wherein the first configuration and the second configuration are different.

7. The method of claim 6 wherein the first configuration has a first absorbent capacity and the second configuration has a second absorbent capacity greater than the first absorbent capacity.

8. The method of claim 1 wherein at least one of the first cut and the second cut form a line of weakness.

9. The method of claim 1 wherein the absorbent layer and the liquid-impermeable layer are joined in facing relation to define an overlap region and wherein the method further includes the steps of, removing a first cut out, a second cut out, a third cut out, and a fourth cut out from the overlap region of the absorbent composite to define a first opening, a second opening, a third opening, and a fourth opening, severing the absorbent composite wherein two of the first opening, the second opening, the third opening, and the fourth opening span only the first cut and wherein two of the first opening, the second opening, the third opening, and the fourth opening span only the second cut.

10. The method of claim 1 wherein the absorbent layer and the liquid-impermeable layer are joined in facing relation to define an overlap region and wherein the method further includes the steps of, removing a first cut out, a second cut out, a third cut out, a fourth cut out, a fifth cut out, a sixth cut out, a seventh cut out, and an eighth cut out from the overlap region of the absorbent composite to define a first opening, a second opening, a third opening, a fourth opening, a fifth opening, a sixth opening, a seventh opening, and an eighth opening, severing the absorbent composite such that none of the first opening, the second opening, the third opening, the fourth opening, the fifth opening, the sixth opening, the seventh opening, or the eighth opening span the first cut or the second cut.

11. The method of claim 10, wherein each of the plurality of discrete absorbent articles include two openings of the first opening, the second opening, the third opening, the fourth opening, the fifth opening, the sixth opening, the seventh opening, and the eighth opening, wherein each of the plurality of discrete absorbent articles have corners including a first corner, a second corner, and a third corner, and wherein the first corner, the second corner, and the third corner of each of the plurality of discrete absorbent articles are adapted to be secured together near a hip of the wearer.

12. The method of claim 1, wherein the plurality of discrete absorbent articles each have side portions and a front portion, the side portions being adapted to be secured together at the front portion near a stomach of the wearer.

13. A method for making multiple absorbent articles comprising, providing a rectangular liquid-impermeable layer having a first length and a first width, providing an absorbent layer having a second length and a second width, joining the absorbent layer and the liquid-impermeable layer in facing relation to define an overlap region of an absorbent composite, severing the absorbent composite at a first cut oriented in a first direction, wherein the first direction is non-parallel with the first width or the first length, severing the absorbent composite at a second cut oriented in a second direction, wherein the second direction is non-parallel with the first width or the first length, removing a first cut out, a second cut out, a third cut out, and a fourth cut out from the overlap region of the absorbent composite to define a first opening, a second opening, a third opening, and a fourth opening, and severing the absorbent composite wherein two of the first opening, the second opening, the third opening, and the fourth opening span only the first cut and wherein two of the first opening, the second opening, the third opening, and the fourth opening span only the second cut.

14. The method of claim 13 wherein the composite is completely severed by the first cut and the second cut to define four discrete absorbent articles having a common junction point.

15. The method of claim 13 wherein the first length is equal to the second length and the first width is greater than second width.

16. The method of claim 14 wherein the four discrete absorbent articles comprise a first pair of absorbent articles having a first configuration and a second pair of absorbent articles having a second configuration wherein the first configuration and the second configuration are different.

17. The method of claim 16 wherein the first configuration has a first absorbent capacity and the second configuration has a second absorbent capacity greater than the first absorbent capacity.

18. The method of claim 13 wherein at least one of the first cut and the second cut form a line of weakness.

19. A method for making multiple absorbent articles comprising, providing a rectangular liquid-impermeable layer having a first length and a first width, providing an absorbent layer having a second length and a second width, joining the absorbent layer and the liquid-impermeable layer in facing relation to define an overlap region of an absorbent composite, severing the absorbent composite at a first cut oriented in a first direction, wherein the first direction is non-parallel with the first width or the first length, severing the absorbent composite at a second cut oriented in a second direction, wherein the second direction is non-parallel with the first width or the first length, removing a first cut out, a second cut out, a third cut out, and a fourth cut out from the overlap region of the absorbent composite to define a first opening, a second opening, a third opening, and a fourth opening, and removing a first cut out, a second cut out, a third cut out, a fourth cut out, a fifth cut out, a sixth cut out, a seventh cut out, and an eighth cut out from the overlap region of the absorbent composite to define a first opening, a second opening, a third opening, a fourth opening, a fifth opening, a sixth opening, a seventh opening, and an eighth opening, severing the absorbent composite such that none of the first opening, the second opening, the third opening, the fourth opening, the fifth opening, the sixth opening, the seventh opening, or the eighth opening span the first cut or the second cut.

20. The method of claim 19 wherein the composite is completely severed by the first cut and the second cut to define four discrete absorbent articles having a common junction point.

* * * * *